(12) United States Patent
Lykke et al.

(10) Patent No.: US 11,534,091 B2
(45) Date of Patent: Dec. 27, 2022

(54) SYRINGE FOR OBTAINING A TARGET VOLUME OF BLOOD

(71) Applicant: Radiometer Medical ApS, Brønshøj (DK)

(72) Inventors: Jacob Lykke, Brønshøj (DK); Louise Wagner Noergaard, Brønshøj (DK); Annika Herlet, Brønshøj (DK); Helene Hoegh Rasmussen, Brønshøj (DK)

(73) Assignee: RADIOMETER MEDICAL APS, Bronshoj (DK)

( * ) Notice: Subject to any disclaimer, the term of this patent is extended or adjusted under 35 U.S.C. 154(b) by 145 days.

(21) Appl. No.: 16/977,916

(22) PCT Filed: Mar. 11, 2019

(86) PCT No.: PCT/EP2019/055943
§ 371 (c)(1),
(2) Date: Sep. 3, 2020

(87) PCT Pub. No.: WO2019/175070
PCT Pub. Date: Sep. 19, 2019

(65) Prior Publication Data
US 2020/0397360 A1 Dec. 24, 2020

(30) Foreign Application Priority Data
Mar. 14, 2018 (DK) .......................... PA 2018 00116

(51) Int. Cl.
*A61B 5/15* (2006.01)
*A61B 5/153* (2006.01)
(52) U.S. Cl.
CPC ........ *A61B 5/150236* (2013.01); *A61B 5/153* (2013.01); *A61B 5/15003* (2013.01); *A61B 5/150824* (2013.01)

(58) Field of Classification Search
CPC .......... A61B 5/150236; A61B 5/15003; A61B 5/150824; A61B 5/153
See application file for complete search history.

(56) References Cited

U.S. PATENT DOCUMENTS 1,863,785 A    6/1932  Dickinson
6,361,505 B1 *  3/2002  Rainen ............... A61B 5/15003
                                                    600/584
(Continued)

FOREIGN PATENT DOCUMENTS

CN    202891951 U    4/2013
CN    205163090 U    4/2016
(Continued)

OTHER PUBLICATIONS

International Search Report for International Application No. PCT/EP2019/055943, dated May 23, 2019 (two pages).
(Continued)

*Primary Examiner* — Daniel L Cerioni
(74) *Attorney, Agent, or Firm* — Finnegan, Henderson, Farabow, Garrett & Dunner, LLP

(57) ABSTRACT

The present invention provides a syringe for obtaining a target volume of a liquid, in particular blood. The syringe provides a piston with a seal having a width that is identical to the volume line indicating the target full volume of the syringe. This offers a precise and an intuitive way for the end user to understand how much blood is recommended to be drawn from the patient. In exemplary embodiments these visual indicators have the same colour and a desired amount of interruptions of the line of the volume scale are provided.

12 Claims, 3 Drawing Sheets

(56) References Cited

U.S. PATENT DOCUMENTS

| | | |
|---|---|---|
| 9,155,840 B1 | 10/2015 | Willis et al. |
| 2008/0287881 A1 | 11/2008 | Kiehne |
| 2013/0310760 A1 | 11/2013 | Ivosevic et al. |
| 2015/0347714 A1 | 12/2015 | Lockhart et al. |
| 2015/0374907 A1* | 12/2015 | Morton ............ A61M 5/14546 604/111 |
| 2016/0166774 A1* | 6/2016 | Leary ............... A61M 5/31568 604/189 |

FOREIGN PATENT DOCUMENTS

| | | |
|---|---|---|
| JP | 2007-190128 A | 8/2007 |
| JP | 2007-260252 | 10/2007 |
| JP | 2010-268883 A | 12/2010 |
| JP | 2018-015427 A | 1/2018 |
| WO | WO 2007/033077 A2 | 3/2007 |
| WO | WO 2015/025300 A2 | 2/2015 |
| WO | WO 2016/100202 A2 | 6/2016 |

OTHER PUBLICATIONS

Written Opinion of the International Searching Authority for International Application No. PCT/EP2019/055943 (six pages).

* cited by examiner

PRIOR ART EXAMPLE

SYRINGE FOR OBTAINING A TARGET VOLUME OF BLOOD

This application is a national stage filing under 35 U.S.C. § 371 of International Application No. PCT/EP2019/055943, filed on Mar. 11, 2019, which claims priority of Danish Patent Application No. PA 2018 00116, filed on Mar. 14, 2018. The contents of these applications are each incorporated herein by reference in their entirety.

FIELD OF THE INVENTION

The present invention relates to syringe technology. In particular, the present invention relates to a syringe for obtaining a target volume of blood and a method of obtaining a target volume of blood.

BACKGROUND OF THE INVENTION

Syringes are used on a daily basis by medical practitioners for handling several different liquids during medical treatments. Typically, syringes are used to obtain blood samples from patients before specific blood tests can be performed. However, medical practitioners often ask themselves how they can make sure that the right blood volume for a specific analysis, not too little, but not too much either, is filled into the syringe. Furthermore, they are concerned how they can know when the piston is aligned correctly to obtain the desired blood volume. The present invention addresses these two end user concerns and will improve the user experience of syringes.

Applicant considers it as especially important to actively approach the above mentioned circumstances, since typically syringes are marketed that are designed to be used in entire systems comprising the syringe, a corresponding analyser, and a corresponding IT solution for carrying out the blood analysis. Typically, the medical suppliers know all the details on how much blood the analysers need to ensure a full palette of test parameters for the recommended maximum time window of, for example, 30 minutes.

It is also often stated by medical suppliers that utmost efforts are made to design medical solutions that help reducing pre-analytical errors, and that they can do this because they understand and influence the entire workflow all the way from drawing blood from the patient until the results are provided to the relevant health care professionals (HCP's).

In this context, the inventors of the present invention have found that the current syringe solutions known to be on the market do not visually or graphically differentiate between general volume indicators on the syringe and an indicator for actually recommended volume. All indicators are of the same thickness, and often kept rather thin, probably to convey a message around precision. To understand the recommended volume, the user will have to refer to the product instructions for use (IFU).

The inventors of the present invention further found that in prior art syringes volume indications are substantially different in thickness compared to the piston seal, which may lead to uncertainty on how to actually align the piston seal. With the prior art syringes, the inventors find it uncertain whether it is the top, the middle, or the bottom of the seal that needs to align with the volume indicator or whether it is the top of the plunger that should align. This may lead to imprecise blood volumes taken from the patient, and this in turn may negatively affect the subsequent analysing procedures.

The present invention addresses these end user concerns identified by the inventors and the present invention will improve the user experience of syringes, especially when a precise volume of blood must be taken to ensure high quality blood analysis results.

SUMMARY OF THE INVENTION

The problem to be solved by the present invention may thus be seen in providing an improved syringe and/or method for obtaining a target volume, particularly a blood volume.

The problem is solved by the subject matter according to the independent claims. The dependent claims, the following description and the drawings show preferred embodiments and further advantages of the invention.

The described embodiments similarly pertain to the syringe and the method. Synergetic effects may arise from different combinations of the embodiments, although they might not be described in detail hereinafter.

Further on, it shall be noted that all embodiments of the present invention concerning the method might be carried out with the order of the steps as described explicitly hereinafter. Nevertheless, this has not to be the only and essential order of the steps of the method described herein. The herein presented method can be carried out with another order of the disclosed steps without departing from the respective method embodiments, unless explicitly mentioned to the contrary hereinafter.

Technical terms are implemented using their common sense. If a specific meaning is conveyed through certain terms, definitions of terms will be given in the following in the context of which the terms are used.

According to the first aspect of the present invention, a syringe for obtaining a target volume of a liquid sample, in particular of blood, is presented. The syringe comprises a housing and a piston within the housing. The housing comprises a first visual indicator for indicating a target volume of blood to be filled into the housing. The piston comprises a second visual indicator. The first visual indicator has a first width and the second visual indicator has a second width which is identical to the width of the first visual indicator. In the context of the present invention the term "visual indicator" may also be understood as "graphical indicator" and is preferably embodied as mark, like e.g. a line, on a volume scale located on the syringe, preferably on or in the housing of the syringe. It is envisaged that the syringe also can be used for obtaining other liquids e.g. urine, milk and/or plasma.

The concept of the present invention allows to visually and intuitively communicate to the user how to align the position of the piston to the volume scale to obtain the recommended and/or desired blood volume for a subsequent analysis. This performed by matching the width of the first visual indicator on the housing with the second visual indicator on the piston. In specific embodiments the first visual indicator may be a line for recommended volume, which is located on the housing, and the second visual indicator is embodied as a seal of the piston. This will be explained hereinafter in more detail in the context of exemplary embodiments.

By matching the width of the first visual indicator on the housing with the width of the second visual indicator on the piston, as shown e.g. in FIG. 2, an intuitive link is created on the syringe for the medical practitioner. When aligned, the first visual indicator and second visual indicator in an embodiment form one solid line on the syringe. Through formative tests performed by the Applicant, this has been shown to provide a strong message to the user that enough volume has been obtained.

Compared to the prior art, the present invention conveys a clear optical feedback to the user on how to align the piston relative to the housing. In an embodiment the target volume may be shown at or close by to the first visual indicator such that the syringe at same time clearly communicates to the user, in the sense of an optical feedback while filling the syringe, how much volume is recommended by the manufacturer of the syringe. In an embodiment, on the syringe of the present invention only the target volume is shown, e.g. as printed text on the housing like e.g. "1.0 mL". This embodiment can be gathered from FIG. 2.

In order to make it easier for the user to see when the target volume, i.e. the recommended/desired volume, has been obtained, no matter how the syringe is oriented, the first visual indicator can be embodied as a line for recommended volume, which extends around the syringe. In preferred embodiment, the first visual indicator is a line on the housing of the syringe for the target volume and the second visual indicator is the piston seal. As is known in the art, such a piston seal, exemplarily shown in e.g. FIG. 2, is used to seal the volume in the housing containing blood from the proximally located volume in the housing, which does not and shall not contain blood. In this embodiment, matching the width of the line for recommended volume to the width of the piston seal provides an intuitive way of communicating to the user how much blood to be aspirated from the patient. The syringe needs less interpretation and less mental effort from the user in order to obtain the correct volume for analysis on a blood analysing device. This emphasises Applicant's focus on reducing pre-analytical errors wherever possible.

It must further be noted that any embodiment of the present invention covers obtaining a volume of liquid, particularly a volume of blood, by using the underpressure created when drawing the piston away from the bottom of the housing. However, the syringe of the present invention also covers so-called "self-filling syringes" where the user starts setting the piston for the intended volume and then fills the syringe by the patients' own blood pressure. As mentioned herein before, the present invention relating to the syringe and the method covers both. Furthermore, generally speaking, the visual indicators used by the present invention may also be seen as graphical indicators positioned on either the housing or the piston, as described herein before in detail.

According to another exemplary embodiment of the invention, the first and second visual indicators have the same colour.

For example, the colour of the circumferential line indicating the target volume on the housing and the colour of the piston seal may be identical. In this embodiment, the piston seal and the line for the target volume will form a solid black line on the syringe, if the colour of the two indicators is chosen as black. This allows easy detection for the user when the desired target volume is obtained. Of course, also other colours like for example white, red, green, blue or any other suitable colour can be used.

According to another exemplary embodiment of the present invention, the first visual indicator is a dotted line with dots having a diameter corresponding to the width of the second visual indicator and the second visual indicator is a sealing element of the piston. When the first visual indicator and the second visual indicator are aligned the user will only see a solid line as the diameter of the dots of the first visual indicator correspond to the width of the second visual indicator.

According to another exemplary embodiment of the present invention, the first visual indicator is a circumferential line extending along the circumference of the housing, and/or wherein the second visual indicator is a sealing element of the piston.

In this embodiment more certainty is provided for the user on how to actually align the piston seal during obtaining the blood volume. The uncertainty caused by prior art devices, whether it is the top, the middle, or the bottom of the seal that needs to align with the volume indicator or whether it is the top of the plunger that should align, is removed. Thus more precise blood volumes can be taken from the patient, and this in turn positively affects the accuracy of the results of the subsequent analysing procedures. These particular advantages and an according embodiment can easily be gathered from the syringe examples shown in FIGS. 2 and 3.

According to another exemplary embodiment of the present invention, the circumferential line comprises a first circumferential section and a second circumferential section. Furthermore, the circumferential line is interrupted twice between the first and second circumferential sections by a first and second interruption. Moreover, the first and second interruptions are located on opposing sides of the syringe's housing.

To align the piston to the indication line, i.e. the circumferential line, it can be important to be able to see both at the same time for the user. Thus, the line is broken in two places in this embodiment. It is broken around the volume mark and on the opposite side of the scale as well, to make the design more tolerant to how the user orients the syringe during operation. This again enhances the optical feedback provided to the user during operation of the syringe.

According to another exemplary embodiment of the present invention, in the first interruption the target volume is printed onto the housing.

The volume text can be placed in the line with a few millimetres of a gap around it, which makes it easy to read and to tie the volume and the circumferential line closely together. FIG. 2 shows this feature for the exemplary target volume of 1.0 mL.

According to another exemplary embodiment of the present invention, the first and second width of the first and second visual indicators are 1 mm, or are between 0.5 and 2 mm, or are between 0.75 and 1.25 mm.

The prior art solutions known to be on the market do not graphically differentiate between general volume indicators on the syringe and an indicator for actually recommended volume. In said prior art, all indicators are of the same thickness and often keep rather thin, probably to convey a message around precision. In contrast thereto, this embodiment of the present invention uses a substantially thicker width for the first and second visual indicators to provide a clear and safe visual feedback to the user. In this way, the alignment between the first and second visual indicator is optically much easier detectable for the user and hence enhances operational accuracy and precision of the syringe.

According to another exemplary embodiment of the present invention, the housing comprises a plurality of additional visual indicators, each indicating a respective volume filled into the housing, but not the target volume. The first visual indicator for indicating the target volume on the housing is different in shape and/or size compared to at least one, preferably to all, visual indicators of the plurality of visual indicators.

In a particularly preferred embodiment, the width of the plurality of additional visual indicators is different to the width of the first and second visual indicators.

According to another exemplary embodiment of the present invention, the first visual indicator indicates a volume of 1.0 mL (millilitre).

According to another exemplary embodiment of the present invention, the piston seal is a rubber O-ring and in a preferred embodiment the O-ring is made of black rubber.

According to another exemplary embodiment, on the syringe only the target volume is shown/indicated, preferably in text form. This embodiment can be gathered from e.g. FIG. 2, where the target volume "1.0 mL" is shown/indicated on the syringe housing as printed text.

According to second aspect of the present invention, a method of obtaining a target volume of blood is presented. The method comprises the first step S1 of providing a syringe according to any of the herein described embodiments and further comprises the step S2 of filling blood into the housing of the syringe until the first and second visual indicators are aligned.

These and other features of the invention will become apparent from and elucidated with reference to the embodiments described hereinafter.

BRIEF DESCRIPTION OF THE DRAWINGS

Exemplary embodiments of the invention will be described in the following drawings. The Figures are only schematic and not drawn to scale.

DETAILED DESCRIPTION OF EMBODIMENTS

Figure 1:
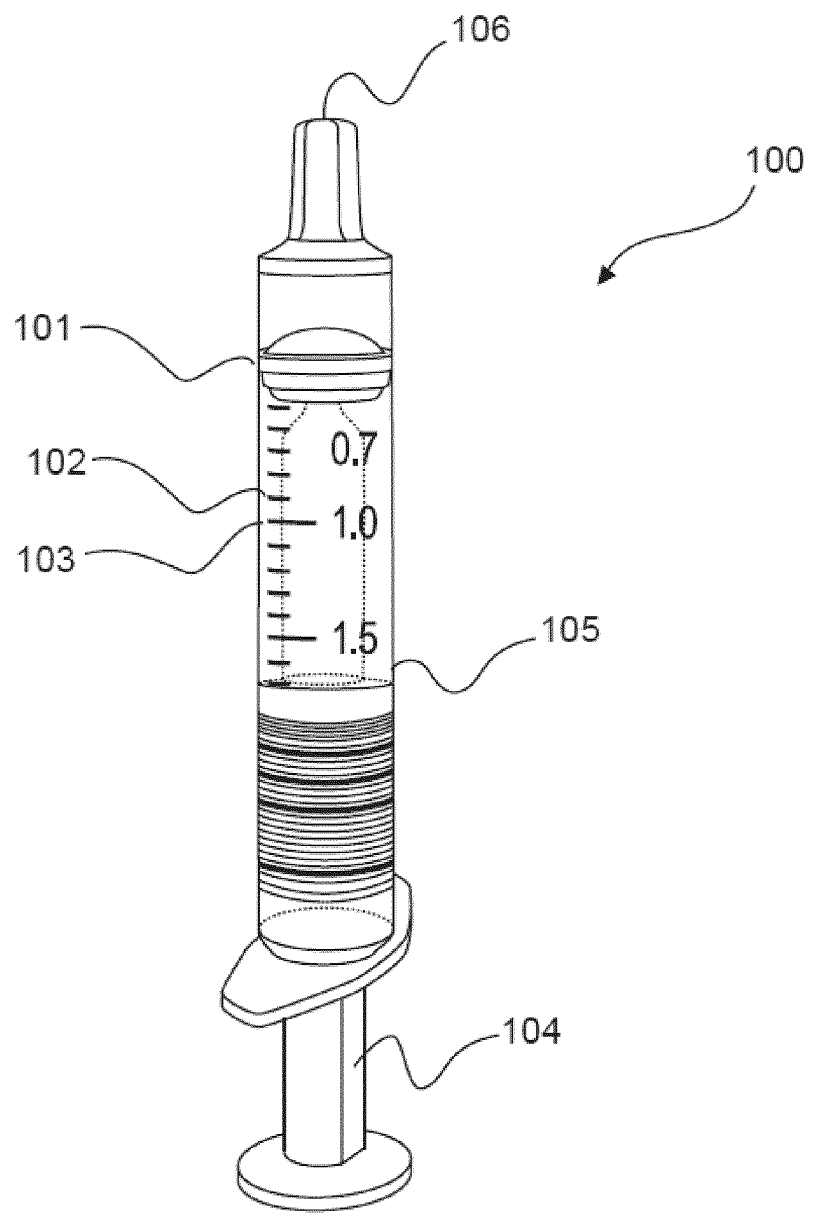
FIG. 1 schematically shows a prior art syringe.

FIG. 1 schematically shows a prior art syringe 100 comprising a body 105 and a piston 104. The prior art syringe 100 comprises a top opening 106. The plunger seal 101 has a much larger width compared to the width of the volume-indicating lines 102 and 103. Assuming that the desired target volume would be 1.0 mL it is clear from FIG. 1 that in the prior art syringe 100, a clear alignment between the thick piston seal 101 and the 1.0 mL mark 103 cannot be precisely achieved by the medical practitioner. The syringe 100 of FIG. 1 does not graphically differentiate between general volume indicators 102 and the indicator for the target volume, here 1.0 mL, as can be seen from the comparison with e.g. the 1.5 mL mark. In addition, the thickness or width of the 1.0 mL mark is identical to the thickness/width of the other volume indicators 102 used on the housing 105.

Figure 2:
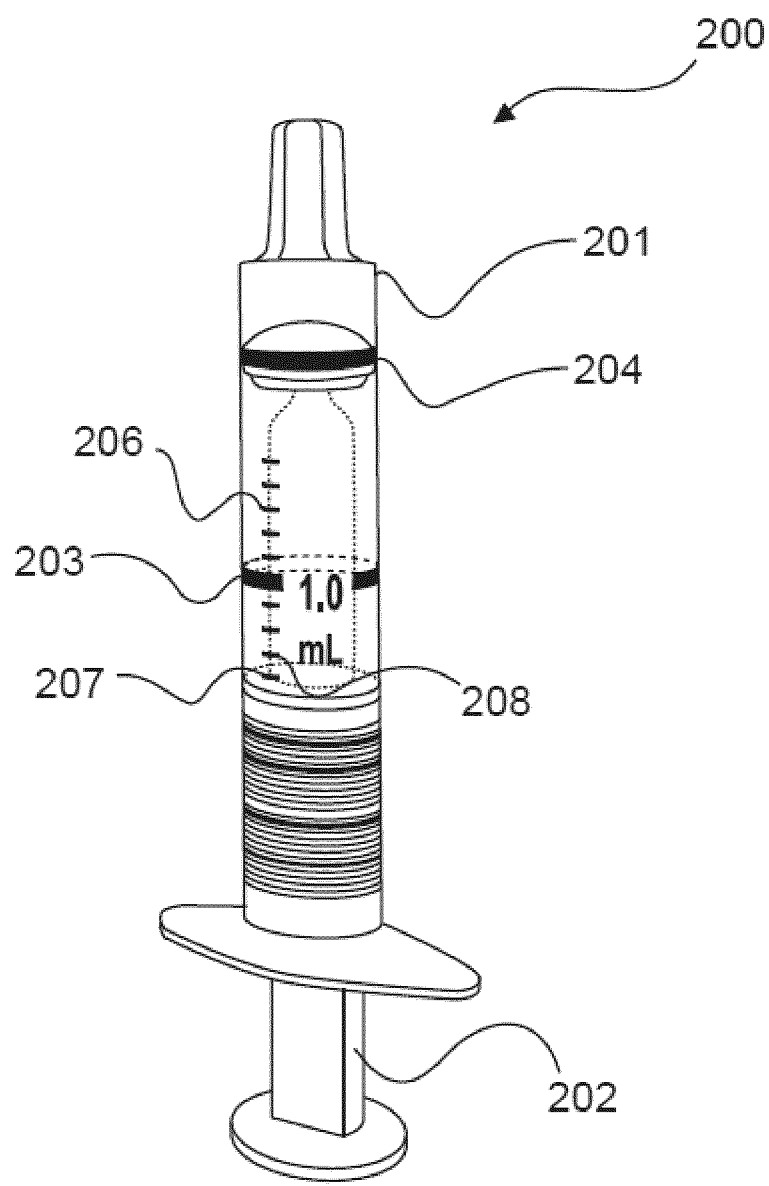
FIG. 2 schematically shows a syringe for obtaining a target volume of blood according to an exemplary embodiment of the present invention.

FIG. 2 schematically shows an exemplary embodiment of a syringe 200 according to an embodiment of the present invention. The syringe 200 comprises a housing 201 and a piston 202 within the housing 201. The housing 201 comprises a first visual indicator 203 for indicating a target volume of blood to be filled into the housing 201. In this exemplary embodiment, the target volume is 1.0 mL. The piston comprises a second visual indicator 204. In the present embodiment, the second visual indicator is embodied as the piston seal in form of a rubber O-ring. As can be gathered from FIG. 2, the first visual indicator 203 has an identical width as the second visual indicator 204. By matching the width of the line for recommended volume, i.e. the target volume, on the scale of the syringe and the width of the piston seal, a strong and intuitive link is created on the syringe for the user. When aligned, the piston seal and the line for the target volume will form a solid black line on the syringe. In this embodiment, on the syringe 200 only the target volume is shown, e.g. as printed text on the housing like e.g. "1.0 mL".

Through formative tests done by the Applicant this has been shown to provide a strong optical signal to the user that enough blood has been obtained in the syringe 200. Compared to the prior art syringe of FIG. 1, the syringe of FIG. 2 provides an approach which conveys a superior message on how to align the piston seal to the volume scale, whilst at the same time clearly communicating how much blood is recommended when filling the syringe.

In a preferred embodiment, the first and second visual indicators have the same colour. As can be seen from FIG. 2, the target volume is printed onto the housing in an interruption of the circumferential line 203. It is also shown that the housing comprises a plurality of additional visual indicators 206, 207 and 208, each indicating a respective volume filled into the housing, which is not the target volume. However, the first visual indicator 203 for indicating the target volume is different in shape and/or size compared to all the other visual indicators. In particular, the first visual indicator has a distinct and different thickness/width compared to the other visual indicators. In this embodiment, the visual indicators are marks on the volume scale positioned on the housing of the syringe. The syringe of FIG. 2 needs less interpretation and less mental effort from the user in order to obtain the correct volume for analysis on a blood analysing device. This emphasises Applicant's focus on reducing pre-analytical errors wherever possible. Further, the syringe of FIG. 2 can be used as both aspirator syringes as well as self-filling syringes.

With the syringe of FIG. 2, the method of obtaining a target volume of blood can be carried out which is inventive over what has been done so far. This method of the present invention comprises the step of the provision of a syringe described herein, for example in the context of FIG. 2 or 3. In a further step, blood is filled into the housing of the syringe until the first and second visual indicators, which have the identical width, align. This procedure ensures a very accurate and precise blood obtaining and hence reduces pre-analytical errors.

Figure 3:
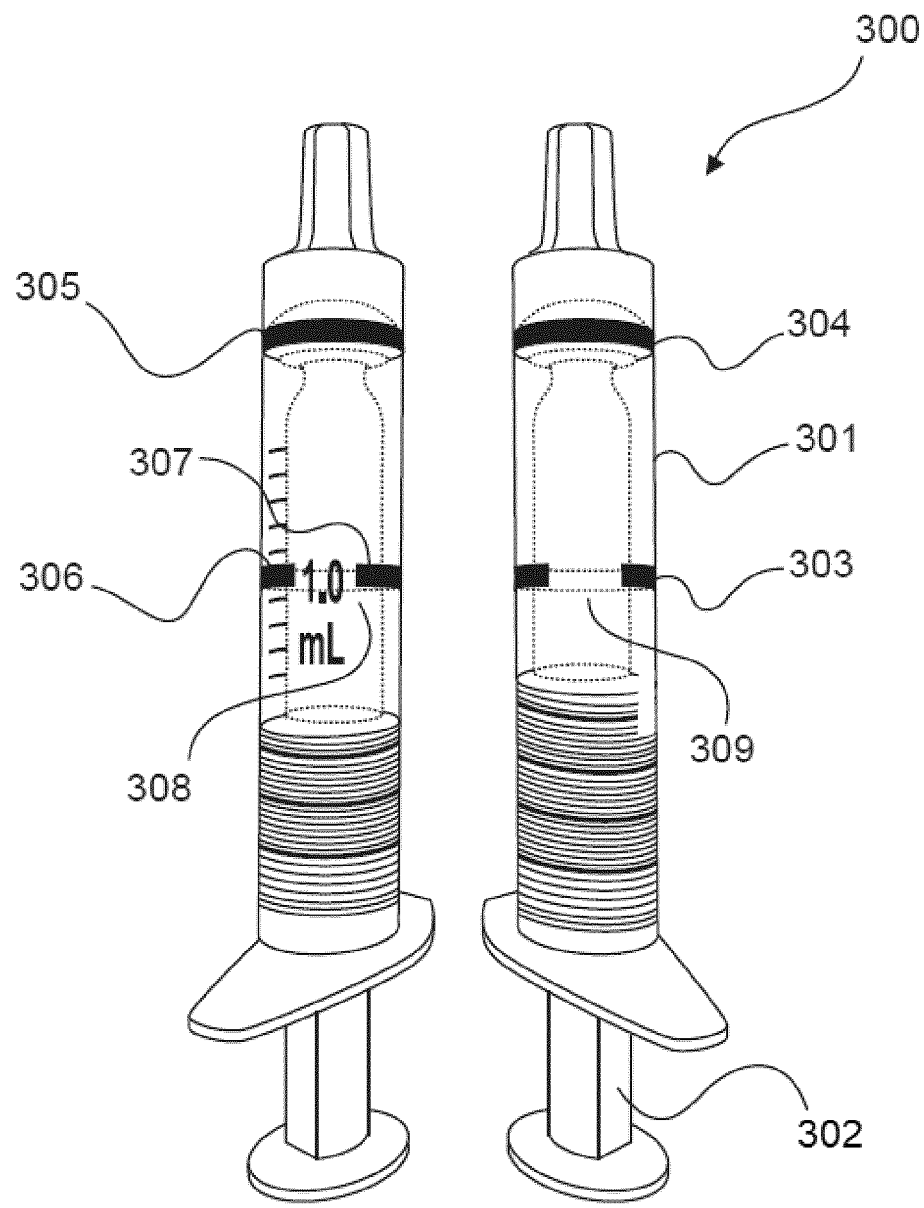
FIG. 3 schematically shows another embodiment of a syringe for obtaining a target volume of blood according to the present invention.

According to another exemplary embodiment of the present invention, FIG. 3 shows a syringe 300 for obtaining a target volume of blood. FIG. 3 shows the syringe 300 from two opposing sides. The housing 301 comprises the piston 302 and has a circumferential line 303 as first visual indicator. The circumferential line 303 comprises a first circumferential section 306 and a second circumferential section 307. In between these sections a first interruption 308 is provided and a second interruption 309 is provided in a second interruption on the opposing side of the housing. In the first interruption 308, the target volume of 1.0 mL is printed onto the housing. In other words, the volume text is placed in the line with a few millimetres of a gap around it making it easy to be read by the user and ties the volume and the indication line closely together. To align the piston 302 to the indication line 303, it is important to be able to see both at the same time. Thus, the line 303 is broken in two places, around the volume mark 1.0 mL and on the opposite side of the volume scale as well, to make the design more tolerant to how the user orients the syringe 300 during aspiration. Also, in this embodiment, the second visual indicator 304 is embodied as the piston seal 305. When aligning the first visual indicator 303 with the second visual indicator 304, 305, a visual and intuitive optical signal is provided to the user that the target volume is obtained. This performed by matching the widths of the line 303 for recommended volume to the width of the piston seal 305.

Other variations to the disclosed embodiments can be understood and effected by those skilled in the art in practicing the claimed invention, from the study of the drawings, the disclosure, and the appended claims. In the claims the word "comprising" does not exclude other elements or steps and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope of the claims.

The invention claimed is:

1. A syringe for obtaining a target volume of blood, the syringe comprising:
   a housing, and
   a piston within the housing,
   wherein the housing comprises a first visual indicator for indicating a target volume of blood to be filled into the housing,
   wherein the piston comprises a second visual indicator, wherein the first visual indicator has a first width,
   wherein the second visual indicator has a second width, wherein the first and second widths are identical,
   wherein the housing comprises a plurality of additional visual indicators each indicating a respective volume filled into the housing, and wherein the width of the plurality of additional visual indicators is different to the width of the first and second visual indicators.

2. The syringe according to claim 1, wherein the first and second visual indicators have the same colour.

3. The syringe according to claim 1, wherein the first visual indicator is a circumferential line extending along the circumference of the housing, and/or
   wherein the second visual indicator is a sealing element of the piston.

4. The syringe according to claim 3, wherein the circumferential line comprises a first circumferential section and a second circumferential section, wherein the circumferential line is interrupted twice between the first and second circumferential sections by a first interruption and a second interruption, and wherein the first and second interruptions are located on opposing sides of the housing.

5. The syringe according to claim 4, wherein in the first interruption the target volume is printed onto the housing.

6. The syringe according to claim 1, wherein the first and second widths are 1 mm.

7. The syringe according to claim 1, wherein the first visual indicator for indicating the target volume is different in shape and/or size compared to at least one of the plurality of additional visual indicators.

8. A method of obtaining a target volume of blood, the method comprising:
   providing a syringe according to claim 1, and filling blood into the housing of the syringe until the first and second visual indicators align.

9. The syringe according to claim 1, wherein the first and second widths range from 0.5 to 2 mm.

10. The syringe according to claim 1, wherein the first and second widths range from 0.75 to 1.25 mm.

11. The syringe according to claim 1, wherein the first visual indicator for indicating the target volume is different in shape and/or size compared to all the plurality of additional visual indicators.

12. The syringe according to claim 1, wherein the first visual indicator is a dotted line with dots having a diameter corresponding to the width of the second visual indicator and the second visual indicator is a sealing element of the piston.

* * * * *